United States Patent
Su et al.

(10) Patent No.: US 7,659,052 B2
(45) Date of Patent: Feb. 9, 2010

(54) MEDIUM COMPRISING CRYOPRECIPITATE AND METHOD FOR PRESERVING PLATELETS, RED BLOOD CELLS AND OTHER CELLS WITHOUT A NUCLEUS

(75) Inventors: Cheng Yao Su, 155 Sec. 2, Li-Lung Street, Pei-Tou District, Hsinchu County (TW); Cheng Chih Lin, 3F, 127, Jiafong 1$^{st}$ Street, Jhubei City, Hsinchu County (TW)

(73) Assignees: Cheng Yao Su, Taipei (TW); Cheng Chih Lin, Jhubei, Hsinchu County (TW)

( * ) Notice: Subject to any disclaimer, the term of this patent is extended or adjusted under 35 U.S.C. 154(b) by 0 days.

(21) Appl. No.: 12/232,482

(22) Filed: Sep. 18, 2008

(65) Prior Publication Data

US 2009/0029342 A1    Jan. 29, 2009

Related U.S. Application Data

(63) Continuation-in-part of application No. 11/157,838, filed on Jun. 22, 2005, now abandoned.

(30) Foreign Application Priority Data

Jun. 29, 2004   (TW) ............................ 93119184 A

(51) Int. Cl.
    *A01N 1/02* (2006.01)
(52) U.S. Cl. ........................................... 435/2
(58) Field of Classification Search ........................ None
    See application file for complete search history.

(56) References Cited

U.S. PATENT DOCUMENTS

| 4,362,567 A | 12/1982 | Schwarz et al. |
| 5,494,590 A | 2/1996 | Smith et al. |
| 5,643,192 A | 7/1997 | Hirsh et al. |
| 5,827,741 A | 10/1998 | Beattie et al. |
| 2006/0009376 A1 | 1/2006 | Eibl |

OTHER PUBLICATIONS

C.R. Valeri, et al., "In vitro testing of fresh and lyophilized reconstituted human and baboon platelets", Transfusion, Oct. 2004, vol. 44, pp. 1505-1512.

P.L. Perrotta, et al., "Platelet Storage and Transfusion", Elsevier Science, Oct. 2002, Chapter 58, pp. 877-905.

R. Cardigan, et al., "Current methods of assessing platelet function: relevance to transfusion medicine", Vox Sanguinis, 2005, vol. 88, pp. 153-163.

*Primary Examiner*—Sandra E Saucier
(74) *Attorney, Agent, or Firm*—Bacon & Thomas, PLLC

(57) ABSTRACT

The present invention provides a platelet-containing composition prepared by contacting platelets with a medium for preserving. The medium comprises anticoagulant, cryoprecipitate and thrombin. The present invention also provides a method for long-term preservation of platelets, comprising the steps of: (a) adding an anticoagulant, cryoprecipitate, thrombin in normal saline; (b) adding a platelet-containing medium into the solution formed in step (a); and (c) lyophilizing the platelet-containing solution formed in step (b). Moreover, the present invention yet provides a medium for preserving non-nucleus cells.

9 Claims, 3 Drawing Sheets

```
┌─────────────────────────────────┐
│    Adding anticoagulants,       │
│  cryoprecipitate, thrombin in   │
│ normal saline and stilling after│
│    shaking to form a solution   │
└─────────────────────────────────┘
```

```
┌─────────────────────────────────┐
│  Adding a platelet-containing   │
│  medium, and stilling to form a │
│   platelet-containing solution  │
└─────────────────────────────────┘
```

```
┌─────────────────────────────────┐
│         Lyophilizing the        │
│  platelet-containing solution   │
│                                 │
└─────────────────────────────────┘
```

Fig. 1

MEDIUM COMPRISING CRYOPRECIPITATE AND METHOD FOR PRESERVING PLATELETS, RED BLOOD CELLS AND OTHER CELLS WITHOUT A NUCLEUS

This patent application is a continuation-in-part (CIP) of U.S. patent application Ser. No. 11/157,838, filed Jun. 22, 2005, entitled "Medium and Method for Preserving Platelets, Red Blood Cells, and Other Non-Nucleus Cells and Platelets-Containing Composition".

BACKGROUND OF THE INVENTION

1. Field of the Invention

The present invention is related to an innovative method and a medium for long-term preservation of platelets, red blood cells (RBC), and other non-nucleus cells in a powdered form. Also provided is a platelet-containing composition, prepared by contacting platelets with the medium for preserving.

2. Description of the Prior Art

Platelets are the smallest circulating blood cells in human body playing the role more than a plug to stop vascular leaks, but also having the ability to release a variety of growth factors that modulate cell growth and promote tissue repair and regeneration.

Since 1960's, scientists have focused attention upon methods of storing platelets in vitro, cumulating with at present an in solution storage capability in a medium of citrated plasma up to 5 days at 22☐ at stable pH levels (pH 6.8-7.2) being achieved. In vitro studies further suggest that storage conveyance technology for platelet concentrates (PCs) is in solution within containers composed of polyolefin for periods up to 5-7 days at room temperature. However, the risk of bacterial contamination in solutions stored at room temperature for this period limits the time during which platelets may be used for transfusion to five days, as established by the FDA.

With blood shortages being increasingly common as the donor base declines and extensive restrictions on blood donation disqualify many donors, red blood cell (RBC) and platelet substitution have long been anticipated as an alternative to standard transfusions.

In particular, a variety of injuries involving excessive bleeding specifically call for the transfusion of platelets. However, due to the degradation of platelet functionality as a consequence current storage technologies, an effective approach for a long-term storage of functionally active platelets has never been succeeded up until now.

Maintaining the normal platelet form in terms of their functional and structural integrity throughout the entire preservation process is of critical importance to ensure their potency when called upon. This is reflected in a preservation process that does not alter the platelet's shape, prevents the excretion of activators and wards off aggregate during preparation and stabilization of the concentration. At molecular level, the ideal preservation process should also retain the glycoprotein Ib/IX, which serves as the receptor for von Willebrand factor, or glycoprotein IIb/IIIa, which serves as the receptor for fibrinogen. It's furthermore necessary for certain metabolic pathways which release messenger substance in response to the bindings of ligands to receptors and which set in motion physiological processes, for example secretion from α-granule, to remain intact. In order to fulfil their normal coagulation function after reconstitution, however, it is crucial to maintain normal intact membranes, functional enzymes, and preserve aggregation, release and phagocytosis responses, i.e. produce viable platelets.

Lyophilization of platelets provides an alternative preserving method that fulfils the above criteria. Lyophilized platelets can be stored at room temperature for an extended period of time and easily reconstituted for use. Moreover, lyophilization improves both shelf life and transportation logistics. In addition, creative approaches to RBC membrane modification, such as the enzymatic cleavage of ABH glycoproteins, may lead to a universal RBC. Advances in the understanding of platelet membrane behaviour at low temperatures may lead to extended platelet storage at refrigerator temperatures.

In view of the drawbacks of current preservation technologies, an effective new method and medium that extends both the quality and duration of the preservation of platelets, RBC and other non-nucleus cells are desperately needed. Therefore, the present invention that facilitates lyophilization of platelets will be a useful alternative for selected clinical applications and will lessen the dependence on marginally adequate blood supplies.

SUMMARY OF THE INVENTION

To address the drawback of known platelets preserving methods, the present invention provides a platelet-containing composition, prepared by contacting platelets with a medium for preserving, the medium comprising:

(a) 5-30 parts by volume of an anticoagulant;

(b) 0.0001-3 parts by volume of cryoprecipitate;

(c) 0.0001-5 parts by volume of a thrombin solution, wherein said thrombin silution is in a concentration of 1000 IU/mL; and (d) 100 parts by volume of normal saline as a solvent.

Another object of the present invention is to provide a method for preserving platelets, comprising:

(a) adding an anticoagulant, cryoprecipitate and thrombin in normal saline and stilling after shaking to form a solution;

(b) adding a platelet-containing medium into the solution formed in step (a) and stilling to form a platelet-containing solution; and (c) lyophilizing the platelet-containing solution formed in step (b).

Yet another object of the present invention is to provide a medium for preserving non-nucleus cells, in which the medium comprising:

(a) 5-30 parts by volume of an anticoagulant;

(b) 0.0001-3 parts by volume of cryoprecipitate;

(c) 0.0001-5 parts by volume of a thrombin solution, wherein said thrombin solution is in a concentration of 1000 IU/mL; and (d) 100 parts by volume of normal saline as a solvent.

Yet another object of the present invention is to provide a pharmaceutical composition, which comprises the platelets-containing composition and a pharmaceutically acceptable carrier.

The inventors of the present invention make use of fibrinogen and thrombin to mimic the last step of haemostasis, and consequently provide a two level solution, firstly a preservation medium and secondly the process to create stable freeze dried powder of platelet-containing compositions allowing for long-term storage.

In the present invention, the preservation 'Cassette' medium wraps the platelets in a protective gel-like film derived from the reaction of adding fibrinogen and thrombin into anticoagulant-containing saline. It is found that it is possible to preserve platelets in a long term, about two years, and still obtain functionally active platelets by utilizing the method and medium disclosed in this invention.

BRIEF DESCRIPTION OF THE DRAWINGS

FIG. 1 shows a flow chart of various steps of the method in preserving platelets of the present invention.

DETAILED DESCRIPTION OF THE INVENTION

Figure 2:
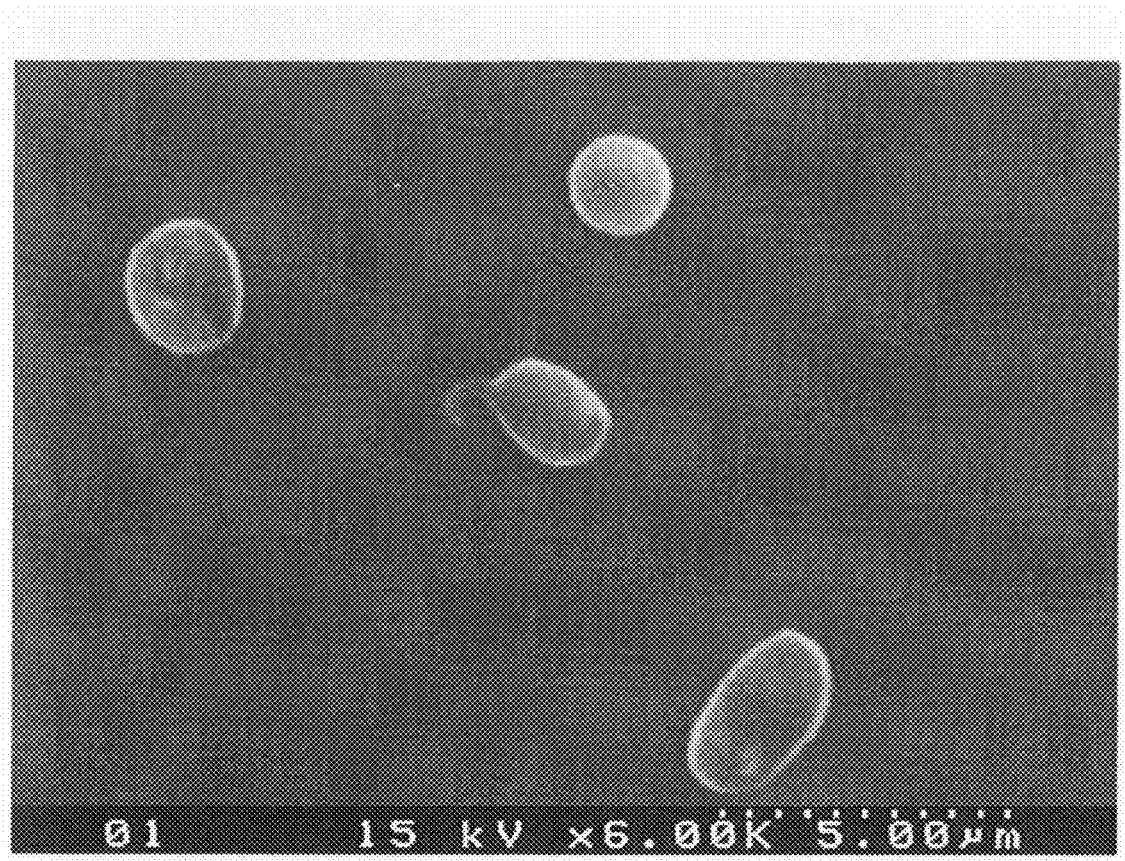
FIG. 2 shows a SEM photo of reconstituted platelets.

As used herein, the term "anticoagulant citrate dextrose solution, formula A" or "ACD-A" means a formulated solution of citric acid, sodium citrate and dextrose in water, which is a common anticoagulant in the blood industry. The formation of ACD-A is listed as below:

| The formulation of ACD-A: | |
| --- | --- |
| Citric acid (anhydrous) | 7.3 g/L |
| Sodium citrate (dihydrate) | 22.0 g/L |
| Dextrose | 24.5 g/L |

As used herein, the term "citrate phosphate dextrose" or "CPD" means a formulated solution of citric acid, sodium citrate, monobasic sodium phosphate and dextrose in water, which is also a common anticoagulant in the blood industry. The formation of CPD is listed as below:

| The formulation of CPD: | |
| --- | --- |
| Sodium citrate (dihydrate) | 26.3 g/L |
| Dextrose (monohydrate) | 25.5 g/L |
| Citric acid (anhydrous) | 3.27 g/L |
| Monobasic sodium phosphate (monohydrate) | 2.22 g/L |

As used herein, the term "cryoprecipitate" is, as defined in hematology, a blood product prepared from fresh-frozen plasma (FFP), which is identified as "the xryoglobulin fraction of plasma obtained by thawing a single donation of FFP at 4±2° C. and removing cryosupernatant (so-called cryopoor plasma)" and in a solution form.

As used herein, the term "thrombin" is a coagulation protein that is able to catalyze many coagulation-related reactions, i.e. converting fibrinogen into fibrin. Thrombin is also known as coagulation factor II.

One of the objects in the present invention is to provide a platelet-containing composition, prepared by contacting platelets with a medium for preserving. The medium comprises 5-30 parts by volume of an anticoagulant; 0.0001-3 parts by volume of cryoprecipitate; 0.0001-5 parts by volume of a thrombin solution, wherein said thrombin solution is in a concentration of 1000 IU/mL; and 100 parts by volume of normal saline as a solvent.

The anticoagulant can be, for example, but not limited to anticoagulant citrate dextrose solution, formula A (ACD-A). Furthermore, the preferable amount of the ACD-A ranges from 5 to 30 parts by volume, more preferable is 10 to 12 parts by volume.

The anticoagulant can be, for example, but not limited to citrate phosphate dextrose (CPD). Moreover, the preferable amount of the citrate phosphate dextrose (CPD) ranges from 5 to 30 parts by volume, more preferable is 10 to 12 parts by volume.

The desirable amount of the cryoprecipitate is 0.001 to 3 parts by volume, more preferable is 0.001 to 0.3 parts by volume.

Preferably, the amount of said thrombin solution is 0.001-5 parts by volume; more preferably, 0.001-0.5 parts by volume.

The composition of the present invention can be manufactured based on the lyophilization technology into powders, or other status by the process that is known to one skilled in the art.

Another object of the present invention is to provide a method for preserving platelets. According to FIG. 1, adding an anticoagulant, cryoprecipitate, and thrombin in normal saline and stilling after shaking to form a solution first. Then, adding a platelet-containing medium into the solution formed in the aforesaid step and stilling to form a platelet-containing solution. Finally, the platelet-containing solution is lyophilized into a dry-powder form.

According to the method of the present invention, the anticoagulant in the solution can be, for example, but not limited to anticoagulant citrate dextrose solution, formula A (ACD-A) or citrate phosphate dextrose (CPD), which is in an amount of 5-30 parts by volume. Moreover, the amount of cryoprecipitate in the solution ranges from 0.0001 to 3 parts by volume. Yet, the amount of the thrombin solution ranges from 0.0001 to 0.05 parts by volume. So called "platelet-containing medium" in the present invention can be platelet concentrate (PC) or platelet-rich plasma (PRP) or any medium that contains platelets.

Yet another object of the present invention is to provide a pharmaceutical composition, which comprises the platelets-containing composition and a pharmaceutically acceptable carrier. The pharmaceutical composition can be further prepared by lyophilization into powders form, or other status by the process that is known to one skilled in the art.

Yet another object of the present invention is to provide a medium for preserving non-nucleus cells. The medium comprises 5-30 parts by volume of an anticoagulant; 0.0001-3 parts by volume of cryoprecipitate; 0.0001-5 parts by volume of a thrombin solution, wherein said thrombin solution is in a concentration of 1000 IU/mL; and 100 parts by volume of normal saline as a solvent.

The anticoagulant can be, for example, but not limited to anticoagulant citrate dextrose solution, formula A (ACD-A). Furthermore, the preferable amount of the ACD-A ranges from 5 to 30 parts by volume, more preferable is 10 to 12 parts by volume.

The anticoagulant can be, for example, but not limited to citrate phosphate dextrose (CPD). Moreover, the preferable amount of the citrate phosphate dextrose (CPD) ranges from 5 to 30 parts by volume, more preferable is 10 to 12 parts by volume.

The desirable amount of the cryoprecipitate is 0.001 to 3 parts by volume, more preferable is 0.001 to 0.3 parts by volume.

Preferably, the amount of sadi thrombin solution is 0.001-5 parts by volume; more preferably, 0.001-0.5 parts by volume.

Besides, so called "non-nucleus cells" means, for example, but not limited to platelets or red blood cells.

The present invention not only opens the possibilities of powdered platelets being not only as a source of multiple growth factors suitable for researches in the field of regenerative medicine but also to help researchers to gain an insight into the characteristics of platelets in vitro. Therefore, the present invention substantially improves traditional platelets-preserving methods.

The advantages of the present invention are further depicted with the illustration of examples. The following is a description of the exemplary case of carrying out the platelets provided by the invention for bioactivity testing. This exemplary case is not to be taken in a limiting sense, but is made merely for the purpose of further illustrating the materials and methods for practicing the present invention.

EXAMPLES

Platelets are enucleated cell fragments and have no mechanism for renewal of expended proteins. When activated or loss of function, they remain non-functional. Although unable to synthesize protein for cell renewal, there are many receptors in a cell surface that play a role in regulating platelet function, and some of the internal proteins can be expressed on the cell surface after activation. In the haemostasis process, platelets adhere, aggregate and form a procoagulant surface leading to thrombin generation and fibrin formation. They contain storage pools of growth factors including PDGF, TGF-$\beta$, VEGF, and EGF as well as cytokines. The following examples make use of the above-mentioned activating characteristic of platelets to detect the activity of reconstituting platelets.

Example 1

Preparation of a Platelets-containing Composition

Preparation of a platelets-containing composition in a powder form (hereinafter refer to "PLT powder"):

(1) adding 20 ml ACD-A (Taiwan Biotech Co., Ltd.) into 100 ml normal saline, then shaking, and stilling for 5 minutes;
(2) adding 0.001 ml cryoprecipitate into the anticoagulant solvent and stilling for 5 minutes after shaking;
(3) adding 5 ml thrombin (in a concentration of 1000 IU/mL, a standard solution produced by Jones Pharma Incorporated), then shaking, and stilling for 5 minutes;
(4) adding platelet concentrate (PC) or platelet-rich plasma (PRP) into a medium processing at step (3), and stilling for 5 minutes; and
(5) finally, the product obtained in step (4) is prepared by lyophilization into powders.

Example 2

Preparation of a Platelets-containing Composition

The process to prepare a platelets-containing composition of the Example 2 is the same with Example 1, except ACD-A adding in step (1) is 5 ml, cryoprecipitate adding in step (2) is 3 ml, and thrombin in step (3) is 3 ml.

Example 3

Preparation of a Platelets-containing Composition

The process to prepare a platelets-containing composition of the Example 3 is the same with Example 1, except ACD-A adding in step (1) is 10 ml, cryoprecipitate adding in step (2) is 0.02 ml, and thrombin in step (3) is 0.01 ml.

Example 4

Assay for P-selectin Expression

Some particular cell surface receptors can be used to estimate the total number of platelets. Likewise, any internal protein that is displayed on the platelet surface after agonist activation may be used to estimate the percentage of cells activated.

"P-selectin" is an internal protein that is exposed on the surface of the platelet after activation. Once, activated, platelets can't be activated again, that is, they are non-functional. Platelets that have aggregated are likewise non-functional. Measurement of P-selectin before and after activation with thrombin provided a measure of the ability of the platelets to be activated.

The experimental step is as follows: 0.001 g PLT powder prepared from example 3 stored for half-year is reconstituted with saline (P) and then adding thrombin which the ratio of P:thrombin equals to 1:1 (v/v). Finally, P-selectin (Cat #BBE6, purchased from R&D system, Inc., Minneapolis, Minn., USA) value is detected in the mixture.

According to Table 1, the P-selectin value of platelet concentrates prepared by platelet pheresis collected from 12 normal donors meeting the requirements of the Chinese Association of Blood Banks for healthy donors is 0.328±0.01 ng/ml. The P-selectin level evaluated from lyophilised reconstituted PLT is 0.34±0.0 ng/ml and that reconstituted PLT mixed with thrombin is 0.35±0.017 ng/ml. It indicates that the reconstituted PLT preserved for half-year still has bioactivity as well as fresh of apheresis platelets. It's concluded that the composition in the present invention can preserve platelets for a long time and retain their functional integrity.

TABLE 1

|  | Apheresis platelets | reconstituted PLT | reconstituted PLT mixed with thrombin |
| --- | --- | --- | --- |
| Volume (PRP)* | 300 ml | 3 ml | 3 ml |
| P-selectin | 0.328 ± 0.01 ng/ml | 0.34 ± 0.0 ng/ml | 0.35 ± 0.017 ng/ml |

*1 g PLT powder is concentrated from 30 ml PRP, and PLT powder used in the example is 0.1 g which equals to 3 ml PRP.

Example 5

Assay for PDGF, TGF-$\beta$, EGF Secretion Materials

Assess growth factor level using ELISA & Activity Assay kits: (PDGF kit & EGF kit purchased from R&D Minneapolis, Minn., USA; TGF-$\beta$1 kit purchased from Biosource International, Nivelles, Belgium)

Human PDGF-AB: Cat #DHD00B (R&D system, Inc., Minneapolis, Minn., USA)

Human TGF-$\beta$1: KAC 1688 (Biosource International, Nivelles, Belgium)

Human EGF: Cat #DEG00 (R&D system, Inc., Minneapolis, Minn., USA)

Experimental Steps:

To observe the bio-activity of reconstituted platelets, the PLT powder prepared from example 3 stored for half-year is taken to mix with normal saline and the proportion is as follows: 0.005 g PLT powder is mixed with saline (p) in a ratio 1:300 (w/v), and the mixture is added with thrombin which the ratio of P and thrombin is 1:1 (v/v).

After reconstituting the platelets, the PLT-saline solvent conducts the ELISA PDGF assay, ELISA TGF-β assay, and the ELISA EGF assay.

Results:

According to Table 2, PDGF value of the control group, thrombin, is 2657.1±887.3 pg/ml; TGF-$β_1$ value of thrombin is 801±20.3 pg/ml, and EGF value of thrombin is too low to be detected. However, it is observed that the amount of PDGF, TGF-β and EGF are larger than the comparative value of thrombin. It's indicated that growth factors including PDGF, TGF-β and EGF which are in their storage pools are certainly secreted from lyophilised PLTs when PLT powder are reconstituted and are mixed with thrombin The results as shown in Table 2 demonstrate that platelets preserving by ways of the present invention, when rejuvenating, still have original function.

In summary, the ELISA data indicate that the composition of platelets preservation in the present invention combined with lyophilization technique can not only preserve platelets for a long time but also keep the bio-activity.

TABLE 2

|  | Control (thrombin) | Reconstituted PLT mixed with thrombin |
|---|---|---|
| PDGF | 2657.1 ± 887.3 pg/ml | 14488.8 ± 887.3 pg/ml (mean ± SD) |
| TGF-$β_1$ (mean ± SD) | 801 ± 20.3 pg/ml | 30913 ± 1141.9 pg/ml |
| EGF (mean ± SD) | ND | 1301.27 ± 1.52 pg/ml |

*pH level: 7.03

Example 6

SEM Examination for Reconstituted Platelets
Experimental Steps

For the sake of observing the morphology in platelets, the reconstituted PLT powder prepared from example 3 stored for half-year conducts a SEM (Scanning Electron Microscope) examination.

The 1 ml solution of 0.1 M phosphate buffer and 5% sucrose (containing 2.5% glutaraldehyde) (pH 7.2) is dripped on a cover glass. And then, PLT powder is mixed with normal saline and taking 0.5 ml to drip on the cover glass. After slow agitating on a shaker for 30 minutes, the cover glass is dehydrated with 50%-100% ethanol. Processed with isoamylacetate, the cover glass is dried in a critical point dryer. Thereafter, the cover glass performs the SEM examination after gold coating.

Figure 3:
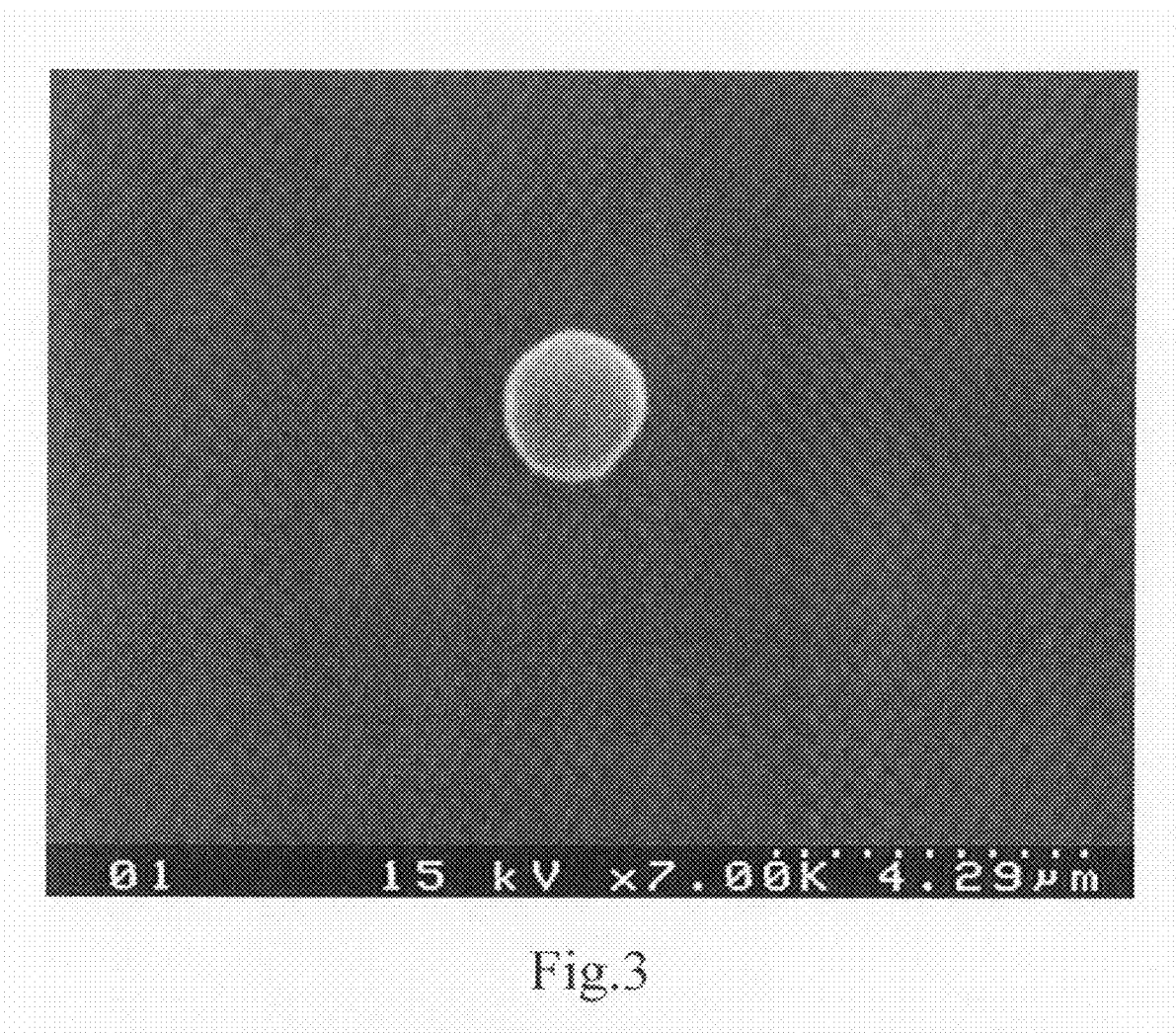
FIG. 3 shows a SEM photo of reconstituted platelets demonstrating a close up view an individual platelet from FIG. 2.

Results:

FIG. 2 of SEM photo shows that the shapes of the reconstituted platelets are thin discs with smooth surface; FIG. 3 shows a close up view from FIG. 2. The morphology of reconstituted platelets indicates that platelets maintain the non-activated characteristics and have the potential to be activated.

Any preserving method must ensure that the platelets retain a certain degree of functional activity, for example, the shape of platelets, that don't excrete activators, and that don't aggregate. According to the method of preservation of the present invention, the platelets present as individual cells and have a predominantly discoid shape. Therefore, it can be concluded that the medium, composition and the method of the present invention are potentially better ways to preserve platelets for a long time and without loss of function.

Other Embodiments

All features disclosed herein may be combined in any form with other methods and replaced by other features with identical, equivalent or similar purpose. Thus except for the part that is specifically emphasized, all features disclosed herein constitute only one embodiment among the numerous equivalent or similar features.

All modifications and alterations to the descriptions disclosed herein made by those skilled in the art without departing from the spirits of the invention and appended claims shall remain within the protected scope and claims of the invention.

What is claimed is:

1. A medium for preserving non-nucleus cells, said medium comprising:
    (a) 5-30 parts by volume of an anticoagulant selected from the group consisting of citrate dextrose solution and citrate phosphate dextrose solution,
    (b) 0.001-3 parts by volume of cryoprecipitate,
    (c) 0.0001-5 parts by volume of a thrombin solution wherein the thrombin solution is in a concentration of 1000 IU/ml, and
    (d) 100 parts by volume of normal saline as a solvent.

2. The medium according to claim 1, wherein the amount of said anticoagulant is 10-12 parts by volume.

3. The medium according to claim 1, wherein the amount of said cryoprecipitate is 0.001-0.3 parts by volume.

4. The medium according to claim 1, wherein the amount of said thrombin is 0.001-0.5 parts by volume.

5. The medium according to claim 1, wherein said non-nucleus cells comprise platelets or red blood cells.

6. A method for preserving non-nucleus cells selected from the group consisting of platelets and red blood cells comprising:
    contacting the cells with the medium of claim 1.

7. A method for preserving non-nucleus cells selected from the group consisting of platelets and red blood cells comprising:
    contacting the cells with the medium of claim 2.

8. A method for preserving non-nucleus cells selected from the group consisting of platelets and red blood cells comprising:
    contacting the cells with the medium of claim 3.

9. A method for preserving non-nucleus cells selected from the group consisting of platelets and red blood cells comprising:
    contacting the cells with the medium of claim 4.

* * * * *